(12) United States Patent
Moriarty et al.

(10) Patent No.: US 8,859,963 B2
(45) Date of Patent: Oct. 14, 2014

(54) METHODS FOR PREPARING THIN SAMPLES FOR TEM IMAGING

(75) Inventors: Michael Moriarty, Portland, OR (US); Stacey Stone, Beaverton, OR (US); Jeff Blackwood, Portland, OR (US)

(73) Assignee: FEI Company, Hillsboro, OR (US)

( * ) Notice: Subject to any disclaimer, the term of this patent is extended or adjusted under 35 U.S.C. 154(b) by 11 days.

(21) Appl. No.: 13/481,351

(22) Filed: May 25, 2012

(65) Prior Publication Data

US 2013/0143412 A1 Jun. 6, 2013

Related U.S. Application Data

(60) Provisional application No. 61/493,308, filed on Jun. 3, 2011.

(51) Int. Cl.
- *G01N 23/00* (2006.01)
- *H01L 21/02* (2006.01)
- *G01N 1/28* (2006.01)
- *H01J 37/305* (2006.01)

(52) U.S. Cl.
CPC .......... *H01L 21/02318* (2013.01); *G01N 1/286* (2013.01); *H01J 2237/31745* (2013.01); *G01N 2001/2886* (2013.01); *H01J 37/3056* (2013.01)
USPC .......... 250/307; 250/360; 250/310; 250/311; 250/492.1; 250/492.3

(58) Field of Classification Search
USPC ............ 250/306, 307, 310, 311, 492.1–492.3
See application file for complete search history.

(56) References Cited

U.S. PATENT DOCUMENTS

| 6,039,000 | A | 3/2000 | Libby et al. |
| 6,042,736 | A | 3/2000 | Chung |
| 7,423,263 | B2* | 9/2008 | Hong et al. .................... 250/304 |
| 7,442,924 | B2* | 10/2008 | Giannuzzi et al. ............. 250/307 |
| 7,675,049 | B2 | 3/2010 | Schmidt et al. |
| 8,163,145 | B2* | 4/2012 | Nadeau et al. ........... 204/298.36 |
| 8,198,603 | B2* | 6/2012 | Takahashi et al. ........ 250/442.11 |
| 2003/0047691 | A1* | 3/2003 | Musil et al. ................. 250/492.2 |
| 2008/0142735 | A1* | 6/2008 | Chandler et al. ........... 250/492.1 |
| 2008/0296498 | A1 | 12/2008 | Hong |
| 2010/0308219 | A1* | 12/2010 | Blackwood et al. .......... 250/307 |
| 2012/0003394 | A1* | 1/2012 | Mulders et al. ............... 427/551 |

FOREIGN PATENT DOCUMENTS

| EP | 2009421 | 12/2008 |
| JP | 11058033 | 3/1999 |

(Continued)

OTHER PUBLICATIONS

Dunin-Borkowski, Rafal E., et al., "Conventional and back-side focused ion beam milling for off-axis electron holography of electrostatic potentials in transistors," Ultramicroscopy, 2005, pp. 67-81, vol. 103.

*Primary Examiner* — Michael Maskell
(74) *Attorney, Agent, or Firm* — Scheinberg & Associates, PC; Michael O. Scheinberg

(57) ABSTRACT

A method and apparatus for preparing thin TEM samples in a manner that reduces or prevents bending and curtaining is realized. Embodiments of the present invention deposit material onto the face of a TEM sample during the process of preparing the sample. In some embodiments, the material can be deposited on a sample face that has already been thinned before the opposite face is thinned, which can serve to reinforce the structural integrity of the sample and refill areas that have been over-thinned due to a curtaining phenomena. In other embodiments, material can also be deposited onto the face being milled, which can serve to reduce or eliminate curtaining on the sample face.

17 Claims, 9 Drawing Sheets

(56) References Cited

FOREIGN PATENT DOCUMENTS

| | | |
|---|---|---|
| JP | 2004286486 | 10/2004 |
| JP | 2007292507 | 11/2007 |
| JP | 2007292507 A * | 11/2007 |
| JP | 2009198412 | 9/2009 |
| WO | 2008049133 | 4/2008 |
| WO | 2008049134 | 4/2008 |
| WO | 2008051937 | 5/2008 |
| WO | 2012103534 | 8/2012 |

* cited by examiner

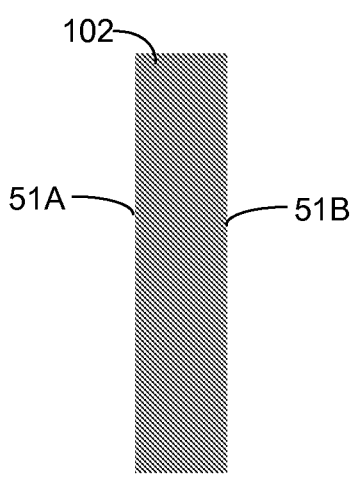 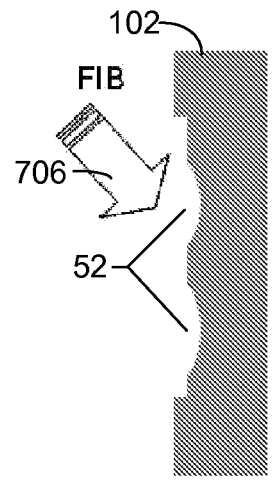
FIG. 5A  FIG. 5B
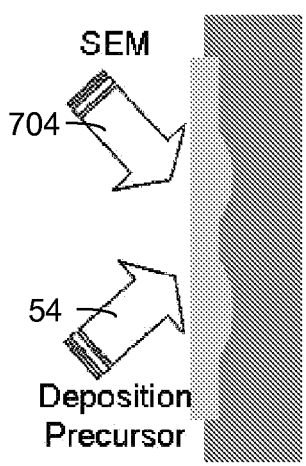 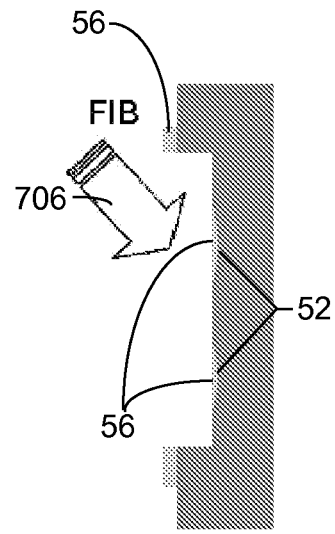
FIG. 5C  FIG. 5D

METHODS FOR PREPARING THIN SAMPLES FOR TEM IMAGING

This application claims priority from U.S. Prov. App. 61/493,308 filed Jun. 3, 2011, which is hereby incorporate by reference.

TECHNICAL FIELD OF THE INVENTION

The present invention relates to preparation of thin samples for transmission electron microscopy and, in particular, to preparation of high quality samples less than 60 nm in thickness.

BACKGROUND OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting lines, spacing and diameter of contact holes, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

Typically, CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

Transmission electron microscopes (TEMs) allow observers to see extremely small features, on the order of nanometers. In contrast to SEMs, which only image the surface of a material, TEM also allows analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site. Samples are typically less than 100 nm thick.

In a scanning transmission electron microscope (STEM), a primary electron beam is focused to a fine spot, and the spot is scanned across the sample surface. Electrons that are transmitted through the substrate are collected by an electron detector on the far side of the sample, and the intensity of each point on the image corresponds to the number of electrons collected as the primary beam impacts a corresponding point on the surface.

As semiconductor geometries continue to shrink, manufacturers increasingly rely on transmission electron microscopes (TEMs) for monitoring the process, analyzing defects, and investigating interface layer morphology. The term "TEM" as used herein refers to a TEM or a STEM, and references to preparing a sample for a TEM are to be understood to also include preparing a sample for viewing on an STEM. In a TEM, a broad beam impacts the sample and electrons that are transmitted through the sample are focused to form an image of the sample. The sample must be sufficiently thin to allow many of the electrons in the primary beam to travel though the sample and exit on the opposite site.

Thin TEM samples cut from a bulk sample material are known as "lamellae." Lamellae are typically less than 100 nm thick, but for some applications a lamella must be considerably thinner. With advanced semiconductor fabrication processes at 30 nm and below, a lamella needs to be less than 20 nm in thickness in order to avoid overlap among small-scale structures. Currently thinning below 60 nm is difficult and not robust. Thickness variations in the sample result in lamella bending, over-milling, or other catastrophic defects. For such thin samples, lamella preparation is a critical step in TEM analysis that significantly determines the quality of structural characterization and analysis of the smallest and most critical structures.

The use of focused ion beam (FIB) systems to create lamellae for TEM microscopy is known in the art. FIB systems are capable of milling lamellae sufficiently thin to be used in a TEM system. The use of dual-beam systems for TEM sample preparation is known in the art. A dual-beam system has a FIB column for milling a lamella from a bulk sample and a SEM column for imaging the lamella, typically as the lamella is being milled. Dual-beam systems improve the time required to prepare samples for TEM analysis. While the use of FIB methods in sample preparation has reduced the time required to prepare samples for TEM analysis down to only a few hours, it is not unusual to analyze 15 to 50 TEM samples from a given wafer. As a result, speed of sample preparation is a very important factor in the use of TEM analysis, especially for semiconductor process control.

FIG. 1 shows a prior art FIB system in an initial orientation for preparing a sample lamella for TEM analysis from a bulk sample material. Bulk sample material 108 is loaded into sample stage and oriented so that its top surface is perpendicular to focused ion beam 104 emitted from a FIB column. A focused ion beam using a high beam current with a correspondingly large beam size is used to mill large amounts of material away from the front and back portion of the region of interest. The remaining material between the two milled rectangles 14 and 15 forms a thin vertical sample section 102 that includes an area of interest. After bulk thinning, the sample section is thinned (typically using progressively finer beam sizes and lower beam energy) until the desired thickness (typically less than 100 nm) is reached. Most of the ion beam machining done to create lamella 110 is performed with bulk sample material 108 and FIB column in this orientation.

Once the specimen reaches a desired thickness, the stage is typically tilted and a U-shaped cut is made at an angle partially along the bottom and sides of the sample section 102, leaving the sample hanging by tabs at either side at the top of the sample. The small tabs allow the least amount of material to be milled free after the sample is completely FIB polished, reducing the possibility of redeposition artifacts accumulating on the thin specimen. The sample section is then further thinned using progressively finer beam sizes. Finally, the tabs are cut to completely free the thinned lamella 110. After thinning the sample is freed from the bulk material at the sides and bottom, and the thinned TEM sample can be extracted.

Unfortunately, ultra thin lamellae formed using the prior art methods described above are subject to undesirable side effects known as "bending" and "curtaining." When attempting to produce ultra thin samples (for example, 30 nm thickness or less) the sample may lose structural integrity and deform under forces acting on the sample, typically by bending or bowing toward one sample face or the other. If this occurs during or prior to a FIB thinning step, then the deformation of the region of interest toward or away from the beam may cause unacceptable damage to the sample.

Thickness variations caused by a milling artifact known as "curtaining" can also have a significant effect on TEM sample quality. When bulk sample material 108 is formed from a heterogeneous structure (e.g., metal gates and shields along with silicon and silicon dioxide), ion beam 104 preferentially mills the lighter elements at a higher mill rate. The heavier metal elements tend to shadow the lighter material underneath them. The resulting effect is a rippled lamella face which is not milled back as far in the areas of metal as it is milled in the areas without metal. FIG. 2 is a photomicrograph of a thinned TEM sample 102 showing curtaining on one sample face, in which the rippled features on the lamella face resemble a hanging curtain. Curtaining artifacts reduce the quality of the TEM imaging and limit the minimal useful specimen thickness. For ultra-thin TEM samples, the two cross-section faces are in very close proximity so thickness variations from curtaining effects can cause a sample lamella to be unusable. Thus, it is desirable to reduce curtaining artifacts during the preparation of TEM sample lamellae.

Although alternatives exist to the curtaining problem, the most effective and widely proven alternative, backside milling, works reasonably well for TEM samples having a thickness of 50 to 100 nm, but for ultra-thin samples having a sample thickness of 30 nm or less, even samples prepared by backside milling often show milling artifacts resulting in an undesirably non-uniform sample face. Further, even for thicker samples, backside milling requires a liftout and inversion operation that is very time consuming. Current backside milling techniques are also performed manually, and are unsuitable for automation.

Thus, there is still a need for an improved method for the preparation of ultra-thin TEM samples that can reduce or eliminate bending and curtaining, and that is suitable for an automated sample preparation process.

SUMMARY OF THE INVENTION

An object of the invention is to provide a method and apparatus for preparing TEM samples less than 60 nanometers thick, more preferably 30 nm or less in thickness, in a manner that reduces or prevents bending and curtaining. Preferred embodiments of the present invention deposit material onto the face of a TEM sample during the process of preparing the sample. In some preferred embodiments, the material can be deposited on a sample face that has already been thinned before the opposite face is thinned, which can serve to reinforce the structural integrity of the sample and refill areas that have been over-thinned due to the curtaining phenomena. In preferred embodiments, material can also be deposited onto the face being milled, which can serve to reduce or eliminate curtaining on the sample face.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIGS. 5A-5I illustrate steps in carrying out the method of FIG. 3.

DETAILED DESCRIPTION OF PREFERRED EMBODIMENTS

Figure 1A:
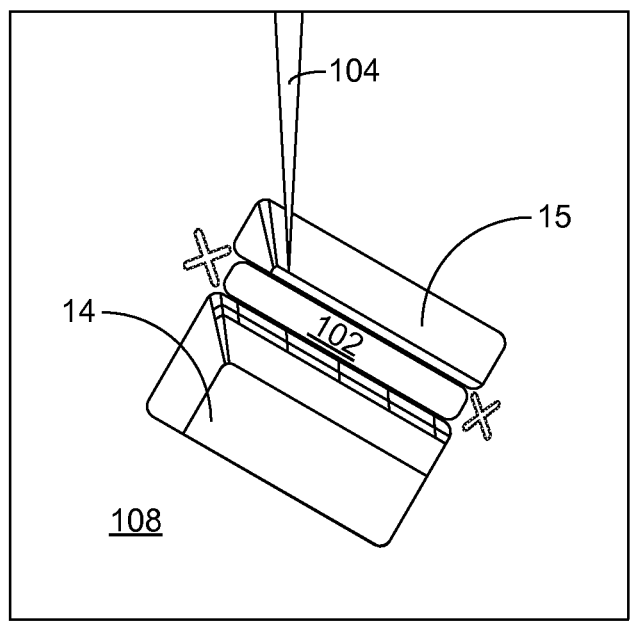
FIG. 1A shows the bulk milling process for preparing a TEM sample from a bulk substrate according to the prior art.

Preferred embodiments address problems of bending and curtaining during TEM sample preparation by adding material to the sample during the process of preparing the sample. In contrast to prior art methods which focus exclusively on removing material from the sample, preferred embodiments of the present invention actually deposit additional material back onto the sample during sample preparation.

In some preferred embodiments, as described in greater detail below, a material can be deposited onto a first TEM sample face after the first face has been thinned, but before the second face is thinned. In some embodiments, all of the deposited material can be left on the thinned first sample face while the second sample face is thinned. In other embodiments, most of the deposited material can be removed from the first thinned side before the second side is thinned. The deposited material left behind can serve to fill in the areas over-thinned by curtaining effects. In either case, the presence of deposited material on the sample face opposite the face being FIB milled can serve to reinforce the structural integrity of the sample.

In some preferred embodiments, material can be deposited onto the sample face as it being thinned. As described above, undesirable curtaining effects often result when a sample is composed of a mixture of more rapidly milling and slower milling materials. Applicants have discovered that by conducting the milling process in the presence of a suitable precursor gas, material can be simultaneously deposited on some parts of the sample surface while other parts of the surface are being milled away. In other embodiments, the sample face can be coated after a fraction of the FIB thinning has been performed on the face. By either or both of these methods, the areas of the sample face having a higher milling rate can be protected or even re-filled by deposited material during the thinning process, thus reducing or preventing curtaining of the sample face.

According to preferred embodiments of the present invention, some or all of the deposited material is removed before sample imaging; in other embodiments the material deposited is sufficiently electron transparent at the desired imaging parameters that it can be left in place during sample TEM analysis. Where some or all of the deposited material is to be removed, any known suitable method can be used for material removal. As will be recognized by persons of skill in the art, a suitable material removal method will depend upon a number of factors such as the material deposited and the structural integrity of the sample. Preferably, the selected material removal method will selectively remove the deposited material causing little if any additional sample material removal from the TEM sample.

It should be noted that the embodiments described above can be used together, separately, or in any desired combination. For example, in some embodiments material will only be deposited onto a sample face after it has been thinned, while in other embodiments material can be deposited both during thinning and after thinning a sample face. A preferred method or apparatus of the present invention has many novel aspects, and because the invention can be embodied in different methods or apparatuses for different purposes, not every aspect need be present in every embodiment. Moreover, many of the aspects of the described embodiments may be separately patentable.

Figure 3:
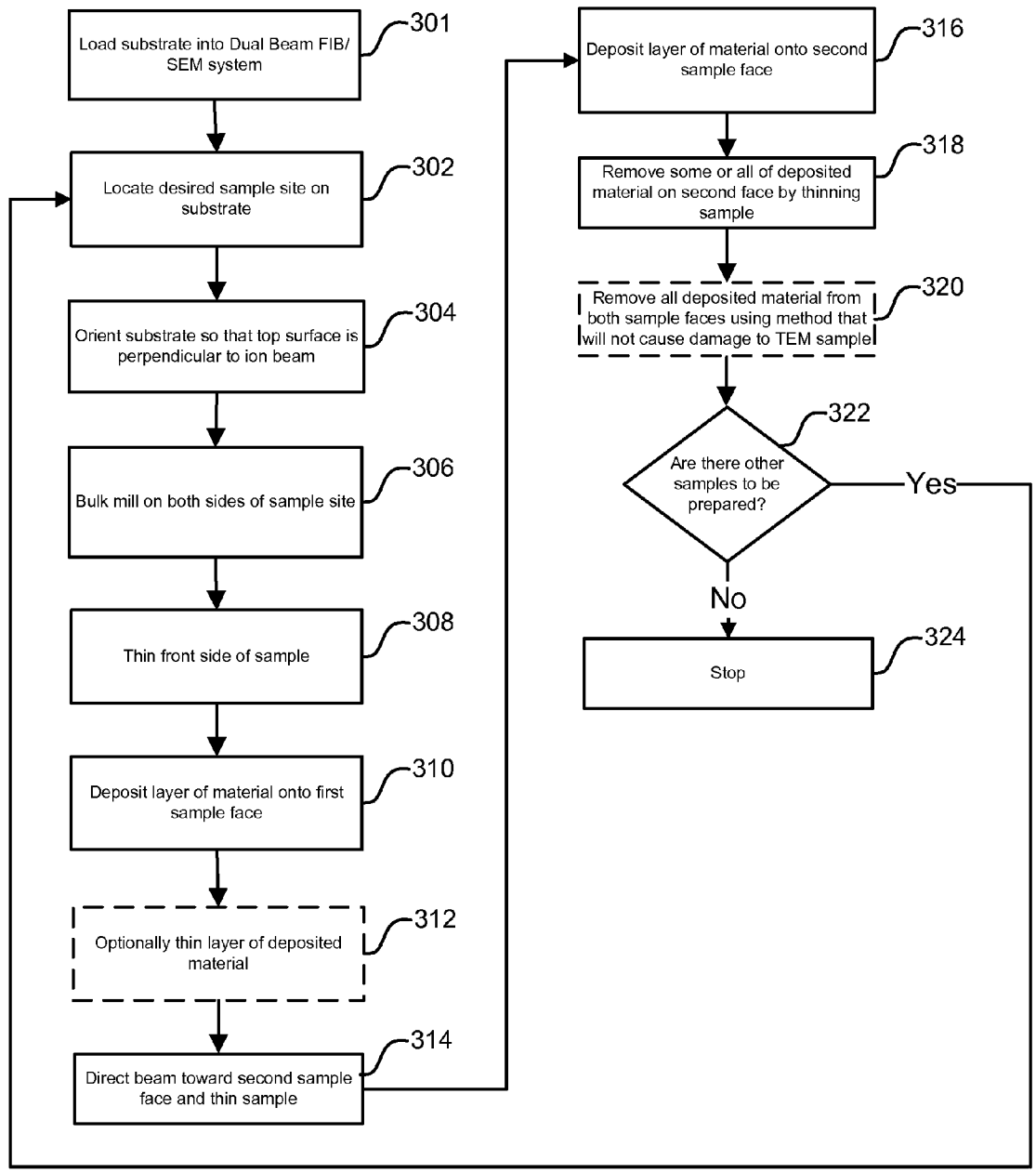
FIG. 3 is a flowchart showing the steps of creating a TEM sample according to a preferred embodiment of the present invention.

FIG. 3 is a flowchart showing the steps of creating a TEM sample according to a preferred embodiment of the present invention. First, in step 301, a substrate such as a semiconductor wafer, a frozen biological material, or a mineral sample is loaded into a suitable processing tool such as a Dual Beam FIB/SEM system having both a FIB column and a SEM column. One such suitable beam FIB/SEM system is the Helios1200 or the Expida™ 1255 DualBeam™ System, available from FEI Company of Hillsboro, Oreg., the assignee of the present invention.

Figure 7:
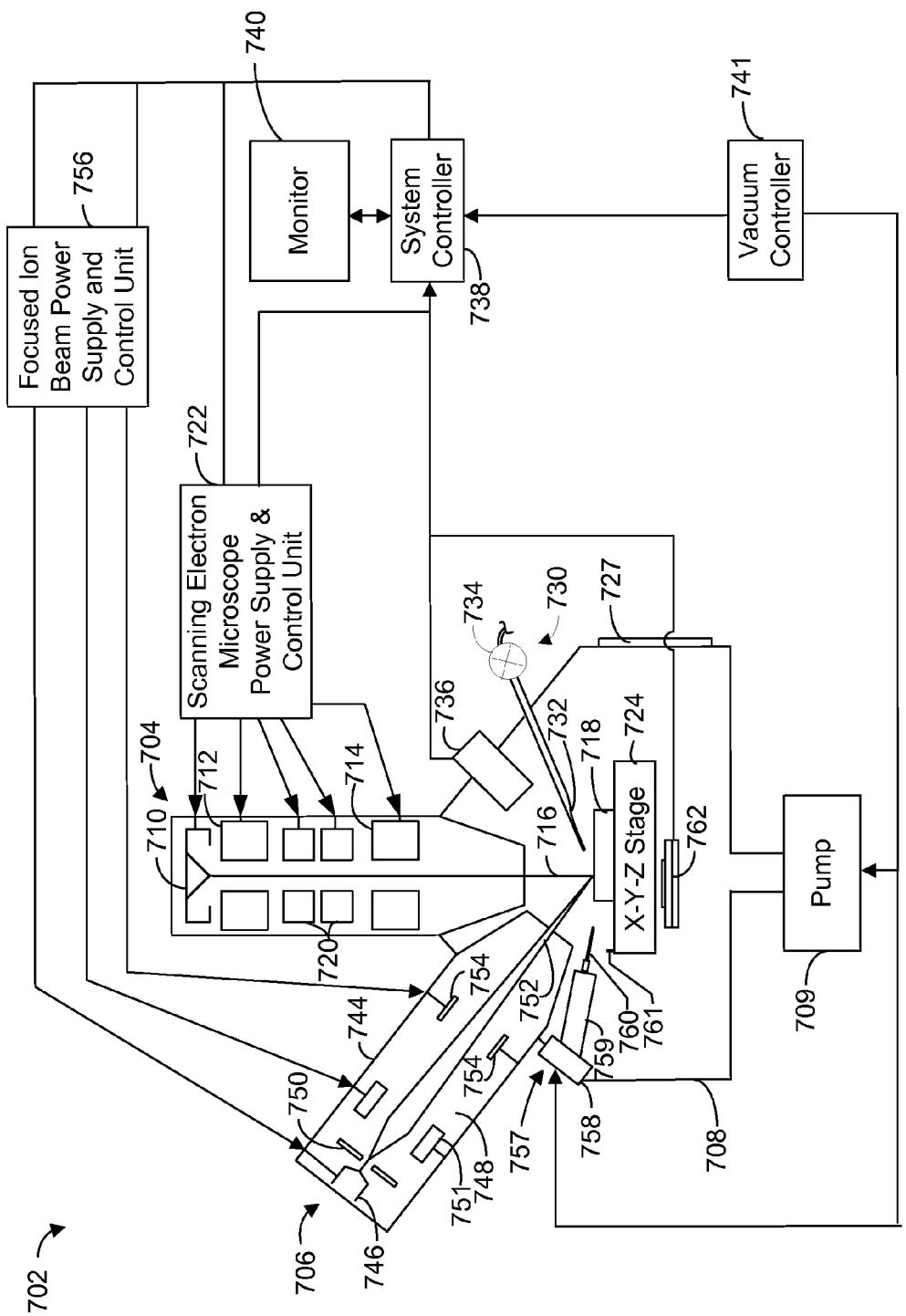
FIG. 7 depicts one embodiment of an exemplary dual beam SEM/FIB system 710 that is equipped to carry out embodiments of the present invention.

Referring also to FIG. 7, the typical dual-beam system 702 configuration is an electron column 704 having a vertical axis with an ion column 706 having an axis tilted with respect to the vertical (usually at a tilt of approximately 52 degrees). Wafers are preferably transferred by way of a multi-wafer carrier and auto-loading robot (not shown), as is well known in the art, although wafers can also be transferred manually.

Figure 4:
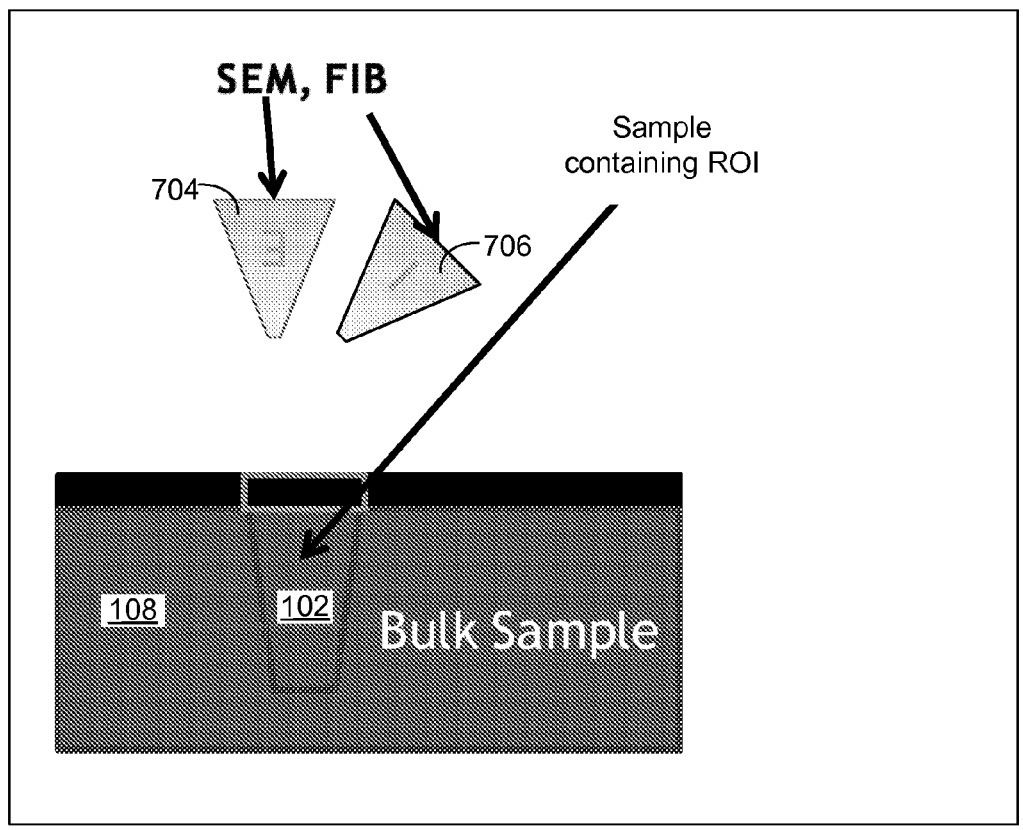
FIG. 4 is a schematic representation showing the location of a sample to be extracted within a larger bulk substrate.

In step 302, the location of a TEM sample (containing a feature of interest) to be extracted from a substrate is determined. For example, the substrate may be a silicon semiconductor wafer or portion thereof and the portion to be extracted may include a portion of an integrated circuit formed on the silicon wafer that is to be observed using the TEM. In other example, the substrate could be a AlTiC wafer and the extracted portion might include a structure used for reading or writing data onto a storage medium. In other example, the substrate could be a sample containing a natural resource and extraction might be performed to analyze characteristics of the resource in the sample. FIG. 4 is a schematic representation showing the location of the sample 102 to be extracted within a larger substrate 108.

In step 304, the substrate is preferably oriented so that its top surface is perpendicular to a focused ion beam emitted from the FIB column 706. A focused ion beam using a high beam current with a correspondingly large beam size is then used to mill large amounts of material away from the front and back portion of a sample section containing the desired TEM sample in step 306. Bulk material removal is preferably performed at high beam current, preferably at highest controllable current available in order remove the bulk material as fast as possible. For example, bulk material removal could be performed using a 13 nA gallium ion beam with a 30 kV accelerating voltage. In some circumstances it may be desirable to mill the substrate with the TEM sample oriented at an acute angle relative to the substrate surface. For example, U.S. Pat. No. 6,039,000 to Libby et al, for Focused Particle Beam Systems and Methods Using a Tilt Column (2000), which is assigned to the assignee of the present invention and hereby incorporated by reference, describes creating a TEM sample using a FIB oriented at an angle relative to the sample surface by etching a cavity on either side of desired TEM sample.

Figure 1B:
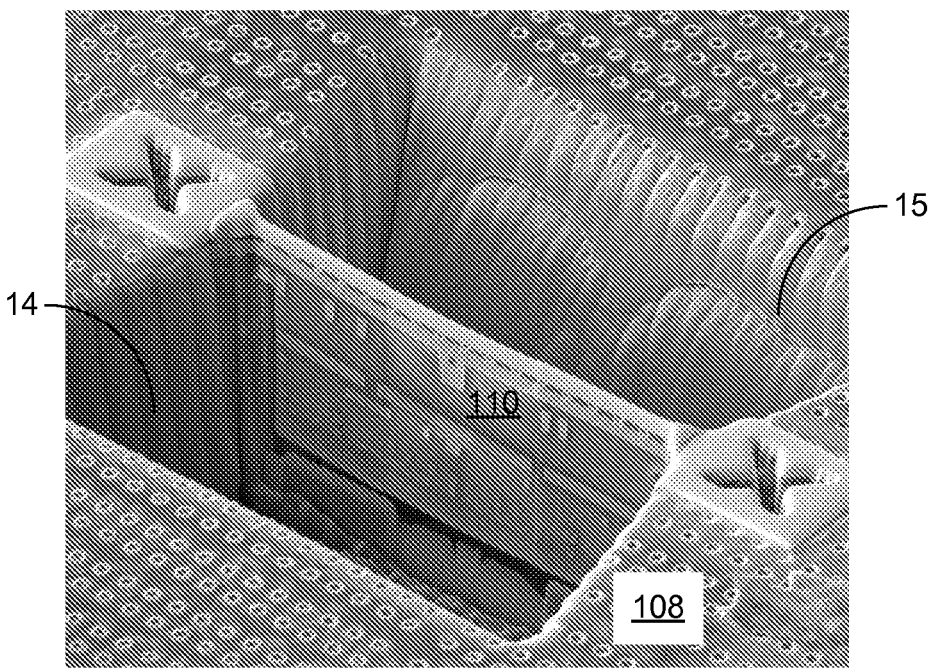
FIG. 1B is a photomicrograph of a thinned TEM sample according to the prior art.
Figure 2:
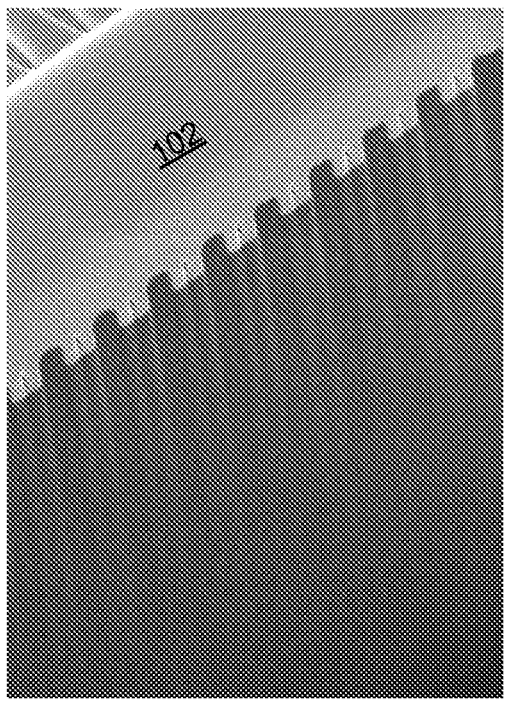
FIG. 2 is a photomicrograph of a thinned TEM sample showing curtaining on one sample face.

As in the prior art method shown in FIG. 1, once the bulk milling is completed, the remaining material between the two milled rectangles 14 and 15 forms a vertical sample section 102, which is still attached to the bulk substrate at the sides and base. FIG. 5A shows such a vertical sample section 102, although none of the surrounding bulk substrate is shown for clarity.

After bulk thinning, in step 308, the sample section 102 is then further thinned on a first side 51A (preferably using progressively finer beam sizes and lower beam energy) until the desired first sample face is reached. For example, the first phase of thinning might use a beam current of 1 nA ion beam, followed by a second phase using a 100 pA beam. As illustrated in FIG. 5B, the exposed first sample face will typically display some degree of curtaining, resulting in over-milled areas 52. The sample is preferably thinned using an ion beam with an axis oriented normal or perpendicular to the top surface of the sample, although a non-normal angle could also be used if the beam axis is oriented to the side of the desired TEM sample face.

Figure 5E:
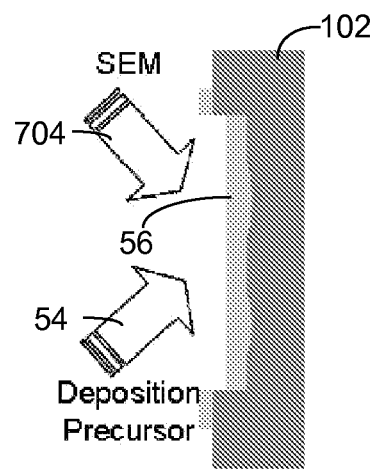

The differences in material thickness shown in FIG. 5B is only for illustration purposes and not intended to show exact scale of difference in thickness between the working surface and the troughs caused by curtaining or to indicate that the surface variations will necessarily be uniform. The arrows indicating the FIB 706 and SEM beam 704 or other processes shown schematically in FIGS. 5B-5I are only intended to illustrate the process being applied, not the angle or orientation of the beams or the exact location of the deposition or etching.

In step 310, once the desired sample face has been exposed, material 56 is deposited onto the exposed sample face. Preferably, a layer of material 56 is deposited onto the entire sample face, for example, by using a precursor gas 54 and chemical vapor deposition, using either the ion beam or an electron beam (depending in part upon the material being deposited). The mechanism for activating the precursors could be SEM, FIB, indirect delivery of secondary particles, or other techniques. Further, the deposition technique is not limited to beam activated precursor deposition.

The material deposited preferably has a different composition than the TEM sample material(s). The choice of material to be deposited may depend upon the particular application of the TEM sample. Suitable deposited materials may include, for example, tungsten, platinum, gold, carbon, silicon oxides, or any other suitable materials. Precursor gases for depositing these materials are well known in the prior art.

Also, as discussed in greater detail below, the deposited material either will be removed during the thinning process or will be easily removable after the critical milling of the TEM sample is completed. For example, where the deposition material is carbon, which can be deposited by carbon vapor deposition, the deposition material can be removed through water vapor etching, which is a very selective etching process that will not cause additional damage to the non-carbon TEM sample. In some preferred embodiments, the deposited material may be one which will not significantly interfere with imaging the TEM sample, in which case it can be left in place. For instance, in applications involving chemical analysis of the sample, the known compounds present in deposited material can be ignored.

In the embodiment shown in FIG. 5C, material 56 is added so that the overall thickness of the original sample section 102 is increased. In other words, more material is added than was removed during the thinning process. This amount of additional material is not required, however, as long as the added material is sufficient to adequately increase the structural integrity of the sample or to fill in a sufficient amount of the curtaining over-milling. The thickness of the deposited layer of thickness depends on how much beam exposure is expected and what material is being deposited. For example, if a Carbon-based material is deposited mainly for the purpose of structural integrity and it will receive minimal erosion from beam exposure, then a deposition layer of approximately 20 nm might be appropriate. If the layer is being used to reduce curtaining during a 1 nA milling step, then a thickness of 100 nm or more might be deposited.

In step 312, a portion of the added material 56 is optionally removed. Because the deposited material is composed of a single compound, little or no curtaining will result as the material is removed. Preferably enough deposited material 56 is left on the sample face 51A to provide additional structural integrity as the other sample face 51B is milled, although all of the deposited material could be removed before proceeding to the second sample face in situations where sample bending is a low priority and the only real concern is the reduction in curtaining. As discussed below, in some preferred embodiments, material can be deposited onto the sample before the final sample face is exposed. The deposited material could then be removed during subsequent additional thinning. The steps of thinning, adding material, and thinning again could be repeated iteratively until the final sample face is exposed. This iterative technique can be useful in minimizing the curtaining effect or if it is desirable can be employed as an end-pointing technique of the thinning step.

Figure 5F:
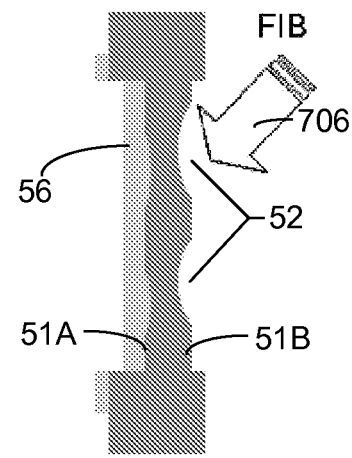
Figure 5G:
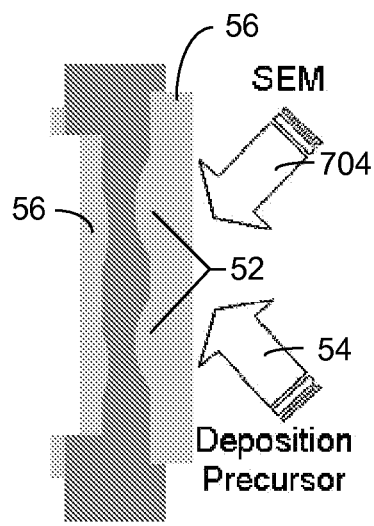
Figure 5H:
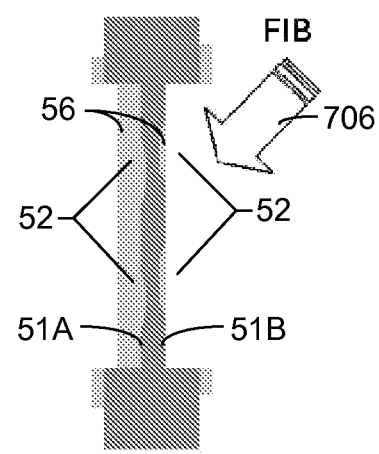
Figure 5I:
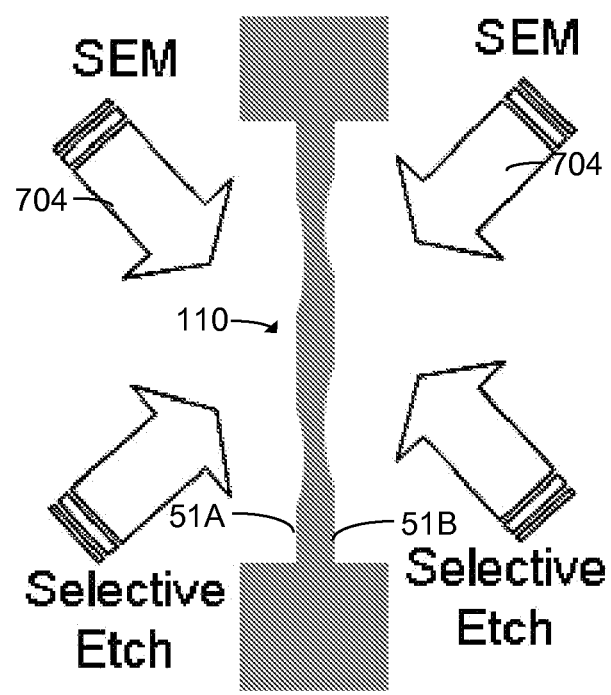

Then, in step 314, the FIB is directed at the second TEM sample face 51B (backside) of sample 102 to thin the sample. Again, progressively finer beam sizes and lower beam energies are used to expose the desired sample face. For example, the first phase of thinning might use a beam current of 1 nA ion beam, followed by a second phase using a 100 pA beam. As illustrated in FIG. 5F, the exposed second sample face 51B will typically also display some degree of curtaining, resulting in over-milled areas 52.

In step 316, material 56 is also deposited onto the second sample face 51B using a suitable process such as chemical vapor deposition. In step 318, some or all of the deposited material on the second face is removed, for example by FIB milling. The material deposited on the backside would also be added and removed iteratively in multiple steps, with all of the material removed on the final thinning step.

Optionally, in step 320, all of the deposited material 56 can be removed from the completed TEM sample 110. The material removal can be accomplished via FIB milling, or by a method that will be less destructive to the TEM sample material such as a selective gas-assisted etching, either with the ion beam or with an electron beam. In other preferred embodiments, the deposited material can be etched away in, for example, an acid bath after the TEM sample is removed from the vacuum chamber. The present invention is not limited to these examples, and any suitable type of beam-based removal or chemistry removal, or plasma induced removal may be utilized. If there are other samples to be extracted from the substrate (step 322) the process returns to step 302 and the next sample site is located. If not, in step 324 the process stops.

In some preferred embodiments of the present invention, material can also be deposited onto the TEM sample face during the thinning process. According to some preferred embodiments, two charged particle beams could be used at one time. For example, in a dual beam system such as the one shown in FIG. 7 below, the electron beam could be used with a suitable precursor gas to deposit the material onto the sample face, while the FIB could be used for milling.

Figure 6:
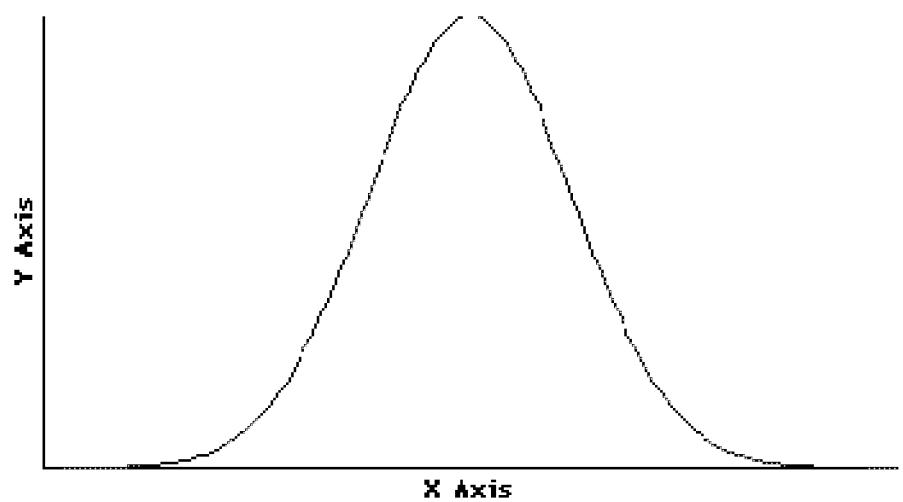
FIG. 6 shows a graph of ion current density versus position along a radial axis for a gallium focused ion beam.

In other embodiments, an ion beam could be used to deposit and remove material at the same time. A focused ion beam system typically has a circularly symmetric, substantially Gaussian current density distribution, as illustrated in FIG. 6, which shows a graph of ion current density versus position along a radial axis. As shown in FIG. 6, the current density at the center of the beam is highest (and thus mills faster) while the beam current tapers off away from the center of the beam.

This beam current spread is one of the main contributors to curtaining. As the beam is milling the lamella face with the center of the beam, the ions in the tail of the Gaussian distribution are reaching sample material in advance of (and behind) the center of the beam. The lower current portion of the beam may have little effect upon the heavier metal sample structures having low milling rates; however, the lighter materials with higher milling rates may be milled to a significant degree.

Applicants have discovered that this "advance" milling can be reduced or eliminated by directing a suitable precursor gas toward the sample surface in the presence of the beam. As is well known in the prior art, when the charged particle beam irradiates the substrate with the adsorbed layer of precursor gas, secondary electrons are emitted from the substrate. These secondary electrons cause a dissociation of the adsorbed precursor gas molecules. Part of the dissociated precursor material forms a deposit on the substrate surface, while the rest of the precursor gas particle forms a volatile by-product and is pumped away by the vacuum system of the apparatus.

In the presence of a suitable precursor gas, the outlying lower current portions of the beam can provide secondary electrons to cause deposition of the dissociated precursor material. This deposited material must then be sputtered away before the underlying substrate is milled. Preferably, the beam current in the center of the beam is high enough to switch the dominant reaction from deposition to milling. In this fashion, the deposited material can serve as a protective layer to prevent significant milling of the lighter, higher milling rate material in advance of the center of the beam, while the center of the beam mills away both the newly deposited protective layer and the underlying substrate at roughly the same rate. Because the beam current is lower at the outlying edges of the beam, the lighter material covered by a protective layer will not etch significantly and curtaining will be prevented or at least substantially reduced. Skilled persons will be able to select a suitable precursor gas and adjust the gas pressure and beam current so that the predominant reaction is deposition at the outlying lower current portions of the beam and etching (milling) at the center of the beam.

In some preferred embodiments, the rate of deposition may be higher than the rate of etching even for the center of the beam so that a protective layer is deposited on the entire surface. The beam parameters or gas pressures can then be adjusted so that etching predominates, either for the entire beam or only for the center high current portion of the beam. Further, according to some embodiments, once some degree of curtaining begins to form during sample milling, the voids in the sample face where the lighter material has been over-milled will tend to have a curved bowl-like shape. Because of the curvature of the walls of the bowls, precursor material will tend to deposit in these regions at a higher rate than on the rest of the sample face. As a result, the beam parameters and precursor gas pressures can be adjusted so that the deposited material will tend to fill in the low areas, thus filling in the curtaining to some degree and protecting the low areas from further over-milling.

Embodiments of the present invention thus provide a means of reducing or preventing sample bending (along with other types of stress-based sample damage) and/or curtaining on the sample face. This is particularly important for ultra-thin samples (defined herein as samples having a thickness of 30 nm or less). Applicants have confirmed experimentally that the deposition of a suitable layer of deposited material on one sample face will allow a silicon TEM sample to be thinned to approximately 30 nm without bending, when similar samples without deposited material had significant bending long before a 30 nm thickness was reached.

Depending upon the particular sample type, it may be more important to avoid one or the other of these types of sample damage. For example, in a sample where the entire structure of interest is less than 100 nm wide, but it sits directly underneath a vertical boundary between a fast milling and slow milling material, curtaining would be the critical type of damage, while sample bending might be irrelevant. In such cases where only one type of damage is important, it may not be necessary to use all of the steps in the method described above. Also, the deposition material does not need to be applied to both faces of a sample. For example, when preparing samples for which bending is the primary concern, it may be sufficient to deposit material only on the first sample face after it is thinned, and then to remove that deposited material after the second sample face is exposed. In some embodiments, the steps of depositing material onto the sample face, and thinning the sample face, then depositing more material onto the sample face may be conducted iteratively until the desired sample thickness has been reached.

The improved structural integrity of the sample being thinned also makes the method of TEM sample production according to the present invention more suited for automated handling and processing, which increases ease of use and can lower cost per sample for our customers. The reduction of curtaining effects allows production of high quality samples with shorter site times and/or greater ease of use than prior art silicon-side milling techniques.

The steps described above can also be applied in any desired order. For example, in some situations it might be desirable to deposit material before any thinning takes place. The sample can also be imaged at any point during the process. Also for example, the deposition of material on the sample face might not be initiated until the sample has been sufficiently thinned and imaging has been performed to recognize the desired features within the sample that will be the targets for the final TEM sample faces. In some preferred embodiments, the material deposition and material removal actions are distinct serial steps. In other embodiments, the deposition and material removal processes can be carried out simultaneously, either on the same face or on different faces, during at least part of the sample preparation.

FIG. 7 depicts one embodiment of an exemplary dual beam SEM/FIB system 702 that is equipped to carry out embodiments of the present invention. Embodiments of the present invention can be used in a wide variety of applications where a low resistivity material is deposited onto a target surface of a substrate. Preparation and analysis of such a sample is typically performed in a dual beam electron beam/focused ion beam system such as the one now described. Suitable dual beam systems are commercially available, for example, from FEI Company, Hillsboro, Oreg., the assignee of the present application. While an example of suitable hardware is provided below, the invention is not limited to being implemented in any particular type of hardware.

Dual beam system 702 has a vertically mounted electron beam column 704 and a focused ion beam (FIB) column 706 mounted at an angle of approximately 52 degrees from the vertical on an evacuable specimen chamber 708. The specimen chamber may be evacuated by pump system 709, which typically includes one or more, or a combination of, a turbo-molecular pump, oil diffusion pumps, ion getter pumps, scroll pumps, or other known pumping means.

The electron beam column 704 includes an electron source 710, such as a Schottky emitter or a cold field emitter, for producing electrons, and electron-optical lenses 712 and 714 forming a finely focused beam of electrons 716. Electron source 710 is typically maintained at an electrical potential of between 500 V and 30 kV above the electrical potential of a work piece 718, which is typically maintained at ground potential.

Thus, electrons impact the work piece 718 at landing energies of approximately 500 eV to 30 keV. A negative electrical potential can be applied to the work piece to reduce the landing energy of the electrons, which reduces the interaction volume of the electrons with the work piece surface, thereby reducing the size of the nucleation site. Work piece 718 may comprise, for example, a semiconductor device, microelectromechanical system (MEMS), data storage device, or a sample of material being analyzed for its material characteristics or composition. The impact point of the beam of electrons 716 can be positioned on and scanned over the surface of a work piece 718 by means of deflection coils 720. Operation of lenses 712 and 714 and deflection coils 720 is controlled by scanning electron microscope power supply and control unit 722. Lenses and deflection unit may use electric fields, magnetic fields, or a combination thereof.

Work piece 718 is on movable stage 724 within specimen chamber 708. Stage 724 can preferably move in a horizontal plane (X-axis and Y-axis) and vertically (Z-axis) and can tilt approximately sixty (60) degrees and rotate about the Z-axis. A door 727 can be opened for inserting work piece 718 onto X-Y-Z stage 724 and also for servicing an internal gas supply reservoir (not shown), if one is used. The door is interlocked so that it cannot be opened if specimen chamber 708 is evacuated.

Mounted on the vacuum chamber are one or more gas injection systems (GIS) 730. Each GIS may comprise a reservoir (not shown) for holding the precursor or activation materials and a needle 732 for directing the gas to the surface of the work piece. Each GIS further comprises means 734 for regulating the supply of precursor material to the work piece. In this example the regulating means are depicted as an adjustable valve, but the regulating means could also comprise, for example, a regulated heater for heating the precursor material to control its vapor pressure.

When the electrons in the electron beam 716 strike work piece 718, secondary electrons, backscattered electrons, and Auger electrons are emitted and can be detected to form an image or to determine information about the work piece. Secondary electrons, for example, are detected by secondary electron detector 736, such as an Everhart-Thornley detector, or a semiconductor detector device capable of detecting low energy electrons. STEM detector 762, located beneath the TEM sample holder 761 and the stage 724, can collect electrons that are transmitted through a sample mounted on the TEM sample holder. Signals from the detectors 736, 762 are provided to a system controller 738. Said controller 738 also controls the deflector signals, lenses, electron source, GIS, stage and pump, and other items of the instrument. Monitor 740 is used to display user controls and an image of the work piece using the signal The chamber 708 is evacuated by pump system 709 under the control of vacuum controller 741. The vacuum system provides within chamber 708 a vacuum of approximately 7×10−6 mbar. When a suitable precursor or activator gas is introduced onto the sample surface, the chamber background pressure may rise, typically to about 5×10−5 mbar.

Focused ion beam column 706 comprises an upper neck portion 744 within which are located an ion source 746 and a focusing column 748 including extractor electrode 750 and an electrostatic optical system including an objective lens 751. Ion source 746 may comprise a liquid metal gallium ion source, a plasma ion source, a liquid metal alloy source, or any other type of ion source. The axis of focusing column 748 is tilted 52 degrees from the axis of the electron column. An ion beam 752 passes from ion source 746 through focusing column 748 and between electrostatic deflectors 754 toward work piece 718.

FIB power supply and control unit 756 provides an electrical potential at ion source 746. Ion source 746 is typically maintained at an electrical potential of between 1 kV and 60 kV above the electrical potential of the work piece, which is typically maintained at ground potential. Thus, ions impact the work piece at landing energies of approximately 1 keV to 60 keV. FIB power supply and control unit 756 is coupled to deflection plates 754 which can cause the ion beam to trace out a corresponding pattern on the upper surface of work piece 718. In some systems, the deflection plates are placed before the final lens, as is well known in the art. Beam blanking electrodes (not shown) within ion beam focusing column 748 cause ion beam 752 to impact onto blanking aperture (not shown) instead of work piece 718 when a FIB power supply and control unit 756 applies a blanking voltage to the blanking electrode.

The ion source 746 typically provides a beam of singly charged positive gallium ions that can be focused into a sub one-tenth micrometer wide beam at work piece 718 for modifying the work piece 718 by ion milling, enhanced etch, material deposition, or for imaging the work piece 718.

A micromanipulator 757, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 757 may comprise precision electric motors 758 positioned outside the vacuum chamber to provide X, Y, Z, and theta control of a portion 759 positioned within the vacuum chamber. The micromanipulator 757 can be fitted with different end effectors for manipulating small objects. In the embodiments described herein, the end effector is a thin probe 760. As is known in the prior art, a micromanipulator (or microprobe) can be used to transfer a TEM sample (which has been freed from a substrate, typically by an ion beam) to a TEM sample holder 761 for analysis.

System controller 738 controls the operations of the various parts of dual beam system 702. Through system controller 738, a user can cause ion beam 752 or electron beam 716 to be scanned in a desired manner through commands entered into a conventional user interface (not shown). Alternatively, system controller 738 may control dual beam system 702 in accordance with programmed instructions. FIG. 7 is a schematic representation, which does not include all the elements of a typical dual beam system and which does not reflect the actual appearance and size of, or the relationship between, all the elements.

Although the description of the present invention above is mainly directed at methods of preparing ultra-thin TEM samples, it should be recognized that an apparatus performing the operation of such a method would further be within the scope of the present invention. Further, it should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

Preferred embodiments of the present invention also make use of a particle beam apparatus, such as a FIB or SEM, in order to image a sample using a beam of particles. Such particles used to image a sample inherently interact with the sample resulting in some degree of physical transformation. Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

Although much of the previous description is directed at semiconductor wafers, the invention could be applied to any suitable substrate or surface. Further, the present invention could be applied to samples that are thinned in the vacuum chamber but removed from the substrate outside the vacuum chamber (ex-situ-type samples) or to samples extracted from the substrate and thinned after mounting on a TEM grid inside the vacuum chamber (in-situ-type samples). Whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . . " The term "integrated circuit" refers to a set of electronic components and their interconnections (internal electrical circuit elements, collectively) that are patterned on the surface of a microchip. The term "semiconductor device" refers generically to an integrated circuit (IC), which may be integral to a semiconductor wafer, singulated from a wafer, or packaged for use on a circuit board. The term "FIB" or "focused ion beam" is used herein to refer to any collimated ion beam, including a beam focused by ion optics and shaped ion beams.

To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of preparing a sample for TEM analysis, the method comprising:
    at least partially separating a sample section containing a feature of interest from a bulk substrate;
    thinning a first side of the sample to expose a first sample face;
    depositing a layer of a material onto the exposed first sample face; and
    thinning a second side of the sample; wherein thinning the first side of the sample to expose the first sample face and depositing the layer of material onto the exposed first sample face is performed simultaneously.

2. The method of claim 1 further comprising depositing a layer of a material onto the exposed second sample face.

3. The method of claim 1 further comprising repeating the steps of thinning a first side of the sample and depositing a layer of a material onto the exposed first sample face until a desired final sample face is exposed.

4. The method of claim 1 in which the sample is prepared using a particle beam system.

5. The method of claim 1 in which the sample is prepared using a focused ion beam system.

6. A method of preparing a sample for TEM analysis, the method comprising:
    loading a sample into the vacuum chamber of a particle beam system;
    at least partially separating a sample section containing a feature of interest from a bulk substrate by particle beam milling;
    thinning a first side of the sample using the particle beam to expose a first sample face;
    depositing a layer of a material onto the exposed first sample face using beam induced deposition;
    thinning a second side of the sample using the particle beam to expose a second sample face; and
    depositing a layer of a material onto the exposed second sample face using beam induced deposition; wherein thinning a side of the sample to expose a sample face and depositing a layer of a material onto the exposed sample face is performed simultaneously for at least one of the first side or the second side of the sample.

7. The method of claim 6 further comprising removing at least a portion of the deposited material from at least one of the first or second sample faces.

8. The method of claim 1 further comprising removing at least a portion of the deposited material.

9. The method of claim 1 in which the method for removing at least a portion of the deposited material comprises removing at least a portion of the deposited material by gas-assisted etching.

10. The method of claim 7 in which removing at least a portion of the deposited material comprises removing at least a portion of the deposited material after the sample is removed from the vacuum chamber.

11. A charged particle beam apparatus, comprising:
a source of charged particles;
a focusing column positioned to receive charged particles from the source and to direct the charged particles toward a sample located inside a vacuum chamber;
a gas injection system for supplying precursor material to the vacuum chamber;
a system controller for controlling the operation of the charged particle beam apparatus in accordance with computer readable instructions; and
a non-transitory computer-readable memory storing computer instructions for:
at least partially separating a sample section containing a feature of interest from a bulk substrate by particle beam milling;
thinning a first side of the sample using the particle beam to expose a first sample face;
depositing a layer of a material onto the exposed first sample face using beam induced deposition, wherein thinning the first side of the sample to expose the first sample face and depositing the layer of material onto the exposed first sample face is performed simultaneously; and
thinning a second side of the sample using the particle beam to expose a second sample face.

12. A non-transitory computer-readable storage medium configured with a computer program, where the storage medium so configured causes a computer to control a charged particle beam system to carry out the steps of the method of claim 6.

13. The method of claim 6 in which the final TEM sample is 30 nm or less in thickness.

14. The method of claim 6 in which the deposited material will not significantly interfere with imaging the TEM sample.

15. A method of preparing a sample for TEM analysis, the method comprising:
at least partially separating a sample section containing a feature of interest from a bulk substrate by particle beam milling;
thinning a first side of the sample using a particle beam to expose a first sample face;
depositing a layer of a material onto the exposed first sample face using beam induced deposition; wherein thinning of the first side of the sample to expose the first sample face and depositing the layer of material onto the exposed first sample face is performed simultaneously; and
thinning a second side of the sample using the particle beam to expose a second sample face.

16. The method of claim 15 further comprising depositing a layer of a material onto the exposed second sample face.

17. The method of claim 16 in which the milling, thinning, and depositing steps occur in a vacuum chamber of a particle beam system.

* * * * *